United States Patent
Papenfuhs et al.

Patent Number: 4,521,617
Date of Patent: Jun. 4, 1985

[54] PROCESS FOR PREPARING PURE ALKYL 1-HYDROXY-2-NAPHTHOATES

[75] Inventors: Theodor Papenfuhs, Frankfurt am Main; Heinrich Volk, Bad Vilbel, both of Fed. Rep. of Germany

[73] Assignee: Hoechst Aktiengesellschaft, Fed. Rep. of Germany

[21] Appl. No.: 585,189

[22] Filed: Mar. 1, 1984

[30] Foreign Application Priority Data

Mar. 4, 1983 [DE] Fed. Rep. of Germany ....... 3307637

[51] Int. Cl.³ .............................................. C07C 51/43
[52] U.S. Cl. ...................................... 562/467; 560/56
[58] Field of Search ........................... 562/467; 560/56

[56] References Cited
U.S. PATENT DOCUMENTS

4,057,576 11/1977 Bachmann et al. ................. 562/467
4,415,750 11/1983 Volk et al. .......................... 562/467

FOREIGN PATENT DOCUMENTS

2911667 2/1980 Fed. Rep. of Germany ...... 502/467

*Primary Examiner*—Paul J. Killos
*Attorney, Agent, or Firm*—Connolly and Hutz

[57] ABSTRACT

A process for preparing pure alkyl 1-hydroxy-2-naphthoates of the formula

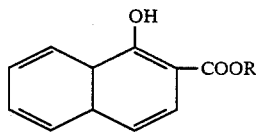

in which R denotes lower alkyl, by adjusting, with mineral acid, to pH 5.5–6.5 an aqueous solution of monoalkali and/or dialkali metal salts of 1-hydroxy-2-naphthoic acid, then adding a surface-active compound (1) of the formula

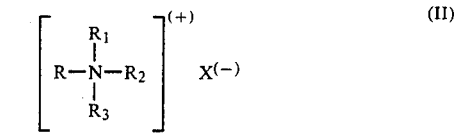

in which R, $R_1$, $R_2$ and $R_3$ denote aliphatic radicals of 1–30 carbon atoms which are substituted and which can contain, in the terminal positions, ionic substituents, or hydroaromatic carbocyclic or cycloaliphatic radicals of 4–8 carbon atoms, and in which $X^{(-)}$ represents one equivalent of an inorganic or organic acid, or (2) of the formula

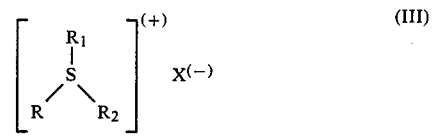

in which R, $R_1$, $R_2$ and $X^{(-)}$ have the abovementioned meanings, the total number of the carbon atoms of R, $R_1$ and $R_2$ being at least 6 and 2 of the aliphatic radicals R, $R_1$ and $R_2$ being able to form, together with the sulfur atom, a heterocyclic ring, or (3) of the formula

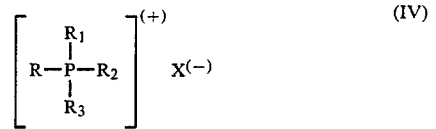

in which R, $R_1$, $R_2$, $R_3$ and $X^{(-)}$ have the meanings given in the definition of the formula (II), the total number of the carbon atoms of R, $R_1$, $R_2$ and $R_3$ being at least 8 and 2 or 3 of the aliphatic radicals R, $R_1$, $R_2$ and $R_3$ being able to form, together with the phosphorus atom, a heterocyclic ring, in an amount of 0.5 to 5% by weight, relative to 1-hydroxy-2-naphthoic acid, separating off the precipitates at 50° C.–100° C., and esterifying the pure monoalkali metal 1-hydroxy-2-naphthoate present in aqueous solution with dialkyl sulfate at pH 5.5–6.5 between 30° C. and 80° C.

1 Claim, No Drawings

PROCESS FOR PREPARING PURE ALKYL 1-HYDROXY-2-NAPHTHOATES

Alkyl 1-hydroxy-2-naphthoates are useful intermediates in the production of dyestuffs and in particular of coloring layers in photographic materials, where they have been able to arouse technical interest for the production of instant pictures and films.

Colorless, crystalline compounds of the formula

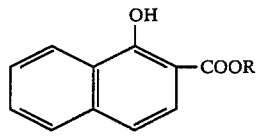

in which R denotes methyl, ethyl, n-propyl, isopropyl, n-butyl or isobutyl, are required chiefly for the last-mentioned field of application, where they need to be free of any impurities, in paticular impurities from the preceding stages of the synthesis, for example free of 1-hydroxynaphthoic acid, 1-alkoxynaphthoic acid and alkyl 1-alkoxynaphthoates, as well as, especially, of higher molecular weight, resinous compounds which are of the type necessarily formed in the industrial production of 1-hydroxynaphthoic acid by carboxylating 1-naphtholates with carbon dioxide using the Kolbe-Schmitt method and which to date cannot be quantitatively removed either in the isolation of hydroxynaphthoic acid or at one of its subsequent stages.

Whereas the level of the first type of impurity can be minimized by means of special synthesis conditions and can be removed completely by recrystallizing the end products of said formula 1, this does not apply to the second type of resinous higher molecular weight impurity. Even repeatedly recrystallizing the end products of said formula (I) in the presence or absence of adsorbents, clarifying auxiliaries and/or reducing or oxidizing agents in no case produces colorless, analytically pure alkyl 1-hydroxy-2-naphthoates as are absolutely necessary for the manufacture of instant picture films. For this reason technically complicated chromatographic methods have had heretobefore to be carried out to obtain the required quality (purity).

It has now been found, surprisingly, that it is possible to prepare pure alkyl 1-hydroxy-2-naphthoates of the general formula (I)

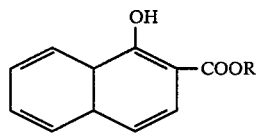

in which R denotes a straight-chain or branched alkyl group of 1 to 5 carbon atoms, in a high yield in a technically simple manner by adjusting, with mineral acid, to pH 5.5–6.5, preferably pH 6.0, an aqueous solution of monoalkali and/or dialkali metal salts of 1-hydroxy-2-naphthoic acid obtained by carboxylating an alkali metal 1-naphtholate [by the Kolbe-Schmitt method; compare in this context BIOS Final Report No. 986, pages 234–249 and 219–225; HOUBEN WEYL 8, 372 et seq. (1952); H. Kolbe, LIEBIGS ANNALEN 113, 125 (1860); R. Schmitt, Berichte der Deutsch. chem. Gesellschaft 20, 2702 (1887)], followed by treatment with water, or by dissolving, in aqueous alkali metal hydroxide solution, 1-hydroxy-2-naphthoic acid prepared in this way but isolated, then adding a surface-active cationic compound (1) of the general formula (II)

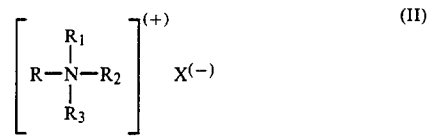

in which R, $R_1$, $R_2$ and $R_3$ each denote identical or different, straight-chain or branched aliphatic radicals of 1 to 30 carbon atoms which are saturated or contain 1, 2 or 3 carbon-carbon double bonds and which can contain 1 to 3 hetero atoms or groupings, such as, for example,

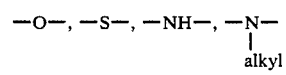

or quaternized nitrogen atoms and/or other groups, such as, for example, carboxamide groups, where the oxygen atom can at the same time be the bridge member between the quaternary nitrogen atom and the aliphatic radical, and which, furthermore, can contain, in terminal positions, ionic substituents, such as, for example, hydroxyl, alkoxy or polyglycol ether groups of preferably 1 to 30 carbon atoms, or hydroaromatic carbocyclic or cycloaliphatic radicals which each have 4 to 8 ring carbon atoms and can bear aliphatic side chains of 1 to 12 carbon atoms or halogen atoms, such as, for example, chlorine or bromine atoms, or aralkyl radicals where the alkyl radical contains 1 to 30 carbon atoms, preferably 1 to 12 carbon atoms, and the aryl radical is a phenyl or naphthyl radical which can be substituted in the aromatic nucleus, for example by hydroxyl groups, lower alkyl groups, lower alkoxy groups and/or halogen atoms, such as chlorine atoms, or aryl radicals, preferably phenyl or naphthyl radicals which can be substituted on the aromatic nucleus by hydroxyl, lower alkoxy, lower alkyl, carboxamide or sulfonamide groups or halogen atoms, such as, for example, chlorine atoms, the total number of the carbon atoms of R, $R_1$, $R_2$ and $R_3$ being at least 8 and two or three of the aliphatic radicals R, $R_1$, $R_2$ and $R_3$ on the quaternary nitrogen atom being capable of forming together with the nitrogen atom a heterocyclic ring which may contain double bonds and onto which a benzene nucleus can be fused, such as, for example, a pyridine, morpholine, imidazoline, benzimidazoline, imidazole, benzimidazole or oxazole ring, and in which $X^{(-)}$ represents one equivalent of an inorganic or organic acid, or (2) of the general formula (III)

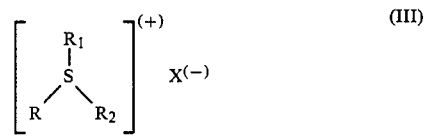

in which R, $R_1$, $R_2$ and $X^{(-)}$ have the meanings mentioned in the definition of formula (II), but where the total number of carbon atoms of R, $R_1$ and $R_2$ is at least 6 and two of the aliphatic radicals R, $R_1$ and $R_2$ together with the sulfur atom can form a heterocyclic ring which may contain double bonds, or (3) of the general formula (IV)

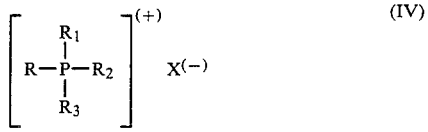

in which R, $R_1$, $R_2$, $R_3$ and $X^{(-)}$ have the meanings given in the definition of formula (II), where the total number of carbon atoms of R, $R_1$, $R_2$ and $R_3$ is at least 8 and two or three of the aliphatic radicals R, $R_1$, $R_2$ and $R_3$ can form together with the phosphorus atom a heterocyclic ring which may contain double bonds, in each case in an amount of 0.5 to 5% by weight, preferably 0.5 to 3% by weight, relative to the amount of 1-hydroxy-2-naphthoic acid present in the solution, separating or filtering off the solid or liquid precipitates quantitatively formed from the resins present at temperatures of 50° C. to 100° C., preferably 70° C.–80° C., if desired after addition of adsorbents, such as active charcoal, and/or filtering aids, such as disperse silicates or aluminum oxides, and esterifying with dialkyl sulfate the pure monoalkali metal salt of 1-hydroxy-2-naphthoic acid present in aqueous solution at pH 5.5–6.5, preferably pH 6.0, and temperature between 30° and 80° C., preferably 40° to 60° C.

In preferred compounds of said formula (II), R is an alkyl radical of 8 to 20 carbon atoms, $R_1$ represents an alkyl radical of 1 to 20 carbon atoms, a hydroxyalkyl radical of 2 to 6 carbon atoms or a phenylalkyl radical of 4 to 12 carbon atoms in the alkyl radical, $R_2$ is an alkyl radical of 1 to 8 carbon atoms or a hydroxyalkyl radical of 2 to 6 carbon atoms, and $R_3$ represents an alkyl radical of 1 to 8 carbon atoms or a benzyl radical.

The following, for example, can be used, according to the invention, as quaternary ammonium compounds of said general formula (II): dodecyldimethylbenzylammonium chloride, oleyltrimethylammonium chloride, distearyldimethylammonium chloride, lauryldimethylhydroxyethylammonium chloride, dodecyldi(hydroxyethyl)methylammonium chloride, dodecyldimethylvinylammonium chloride, dodecylmethylmorpholinium chloride, laurylpyridinium chloride, hexadecyl-N,N'-dimethylbenzimidazolinium sulfate, dodecyldi(triethylene glycol ether)benzylammonium chloride, phenylnonyldimethylbenzylammonium chloride, oleyldi(hydroxyethyl)ethylene glycol ether ammonium chloride, oleyldimethylhydroxyethylammonium chloride, cocosdi(triethylene glycol ether)benzylammonium chloride, cocosdimethylbenzylammonium chloride, distearyldimethylammonium chloride, trioctylmethylammonium chloride, cocosdimethylhydroxypropylammonium chloride, p(isobutyl)phenoxyethoxyethyldimethylbenzylammonium chloride, oleylmethylimidazolinium chloride, hexadecyl-N,N'-dimethylbenzimidazolinium sulfate, oleylmethylimidazolium chloride and dehydroabietyldimethylbenzylammonium chloride. (For the purposes of this invention, the radical "cocos" is an aliphatic radical comprising a mixture of alkyl, alkenyl and alkdienyl radicals of 8 to 18 carbon atoms each).

The following are examples of phosphonium compounds of said general formula (IV) which can be used in the invention: trioctylmethylphosphonium chloride, phenylnonyldimethylbenzylphosphonium chloride, dodecyldimethylbenzylphosphonium chloride, lauryldimethylhydroxyethylphosphonium chloride, tridecylmethylphosphonium chloride, distearyldiethylphosphonium chloride and oleyltrimethylphosphonium chloride.

The aqueous solutions of pure monoalkali metal salts of 1-hydroxy-2-naphthoic acid which are obtained in the course of the process according to the invention can of course be used, by adding mineral acids, for separating off uncontaminated 1-hydroxy-2-naphthoic acid which is particularly useful in any subsequent reactions desired. However, in the further processing according to the invention, namely in the esterification with dialkyl sulfates, the aqueous solution is preferably used directly, which saves the additional isolating step and thus avoids potential deterioration in quality (for example by washing with technical-grade water and possibly storing and/or drying).

The esterification advantageously takes the form of reacting the aqueous monoalkali metal salt solution of 1-hydroxy-2-naphthoic acid, which has been freed of resins according to the invention, at 30°–80° C., preferably 40° to 60° C., and at pH 5.5–6.5, preferably pH 6.0, by simultaneous addition of dialkyl sulfate and an alkali metal hydroxide solution while keeping the pH constant. The excess of alkylating agent is subsequently destroyed by adding ammonia, and, if desired after an intermediate clarification with active charcoal and/or lightening with a conventional bleaching agent, such as sodium dithionite, the end product is precipitated with mineral acid at a pH of about 7–8.5, is filtered off and, if desired, is dried.

The dialkyl sulfates are preferably technically readily accessible compounds, such as, for example, dimethyl sulfate and diethyl sulfate.

If desired, the water-moist or dried alkyl 1-hydroxy-2-naphthoate obtained according to the invention can be recrystallized from alkanols, preferably from whichever alkanol corresponds to the alkyl ester group of the product to be recrystallized, in order to improve its appearance (crystallinity) and/or increase the quality (removal of any free 1-hydroxy-2-naphthoic acid present).

Analytically pure alkyl 1-hydroxy-2-naphthoates which are highly suitable for use in photographic layers are thus obtained in very high yield in a techniclly simple manner in which the aqueous alkali metal 1-hydroxy-2-naphthoate solution obtainable by carboxylating alkali metal 1-naphtholate and subsequent treatment with water may be used directly and the target products can hence be prepared in a technically optimal manner in a single-vessel reaction starting from 1-naphthol and eliminating the need for regenerations, filtrations, dryings and the technically complicated apparatus required for those operations.

It is true that the esterification of 1-hydroxy-2-naphthoic acid with dialkyl sulfate in alkaline solution is known in principle (H. Kaufmann, M. Egner, B. 46, 3782 (1913)), but the literature contains nothing about yield and quality. Only maintenance of narrow, defined pH and temperature conditions permits selective esterification of the carboxyl group without any etherification of the competing hydroxyl group [Luxembourg Patent No. 71, 834].

However, alkyl 1-hydroxy-2-naphthoates thus prepared always contain (in addition to the resins which are contained in the starting material which can only be removed by the process according to the invention) still unconverted 1-hydroxy-2-naphthoic acid, from which, however, they can be freed by single recrystallization from alkanols, advantageously, in order to exclude the danger of transesterification, from the alkanol corresponding to the ester group.

The cationic, surface-active compounds of the general formulae II, III and IV used according to the invention and the resins present in 1-hydroxy-2-naphthoic acid from the synthesis surprisingly produce quantitative water-insoluble precipitates which, depending on the precipitation temperatures chosen and depending on the structure of the surface-active compound, are in solid or liquid form, but otherwise the nature of these resin precipitates is unknown.

These quantitative precipitations must be regarded as surprising insofar as cationic, surface-active compounds covered by the abovementioned general formula (II) are used in the process of German Auslegeschrift No. 1,643,541 to keep in solution the impurities contained in carboxylation product mixtures obtained from phenolate carboxylations following mixing with water and subsequent acidification for precipitation of the desired hydroxybenzoic acid, and to avoid precipitating these impurities together with the desired hydroxybenzoic acid.

The following examples are intended to illustrate the present invention without limiting it.

EXAMPLE 1

882 parts of a dark brown aqueous solution of disodium 1-hydroxy-2-naphthoate prepared by carboxylating sodium 1-naphtholate and subsequently dissolving the carboxylation melt in water, the solution containing 188 parts of free 1-hydroxy-2-naphthoic acid, are brought to pH 5.5 by adding about 100 parts of concentrated sulfuric acid.

The mixture is heated with stirring to about 60° C., 1.8 parts of cocosbenzyldimethylammonium chloride are added, and the mixture is stirred at 60° C. for 5 minutes.

The blackish brown precipitate is filtered off, and 277 parts of dimethyl sulfate are added at 55°-60° C. to the clear, water-bright filtrate in the course of 3 hours. The pH is maintained at 5.5 by simultaneously adding 200 parts of 33% strength sodium hydroxide solution. The mixture is stirred for 30 minutes, 100 parts of water and 22 parts of 25% strength aqueous ammonia are added in succession, and the mixture is stirred at 55°-60° C. for a further hour and is then cooled down to 20° C.

The precipitated methyl ester of 1-hydroxy-2-naphthoic acid is filtered off with suction, washed with water until neutral, and dried. This gives 195 parts having a melting point of 75.5°-76.5° C., corresponding to a yield of 96.5% of theory, relative to 1-hydroxy-2-naphthoic acid (purity as determined by potentiometric titration: 99.8%).

The colorless crystalline product thus prepared, in addition to small amount (0.1-0.2%) of 1-hydroxy-2-naphthoic acid, contains no impurities whatsoever. The small amounts of 1-hydroxy-2-naphthoic acid can likewise be quantitatively removed by simple recrystallizatiion from 5-6 times the amount of methanol (melting point then 76.5°-77° C.).

If the cocosbenzyldimethylammonium chloride is replaced by 2.0 parts of phenylnonyldimethylbenzylphosphonium chloride and the procedure used is otherwise as given above, this produces the methyl ester of 1-hydroxy-2-naphthoic acid in comparable yield and quality.

COMPARATIVE EXAMPLE

If Example 1 is repeated without, however, the addition of cocosbenzyldimethylammonium chloride, this gives in comparatible yield a dark brown methyl ester of 1-hydroxy-2-naphthoic acid which has a melting point of 69°-72° C. (purity as determined by potentiometric titration: 96.5-97%) and cannot be obtained in colorless form and free of impurities even by means of 5 wasteful recrystallizations from methanol in the presence of active charcoal.

EXAMPLE 2

188 parts of technical 1-hydroxy-2-naphthoic acid are dissolved at 90° C. in a mixture of 120 parts of 33% strength sodium hydroxide solution and 520 parts of water. The solution is then cooled down to 75° C. and is brought to pH 6 by adding 1.9 parts of concentrated sulfuric acid.

4.0 parts of trioctylmethylammonium chloride are added to the dark brown solution. This is followed, 10 minutes later, by 5 parts of active charcoal and 5 parts of a mineral filtering aid, and the mixture is stirred for a further 5 minutes and is filtered through a preheated suction filter. The colorless clear filtrate is cooled down to 40° C. 252 parts of dimethyl sulfate are added dropwise at a uniform rate in the course of one hour, during which the pH is maintained at 6.0 by simultaneously adding 120 parts of 33% strength sodium hydroxide solution.

During this addition the methyl ester of 1-hydroxy-2-naphthoic acid precipitates in the form of colorless crystals. The mixture is stirred for 3 hours, is brought to pH 10.0 by adding 6 parts of 33% strength sodium hydroxide solution, is stirred for a further hour and is then cooled down to 20° C. The precipitate is then filtered off with suction, washed with water until neutral, and dried. This gives 191 parts of methyl 1-hydroxy-2-naphthoate which has a melting point of 76°-77° C. and is free of any detectable impurities (purity as determnined by potentiometric titration: 99.9-100%; yield: 94.6% of theory, relative to 1-hydroxy-2-naphthoic acid). If the sodium hydroxide solution is replaced by corresponding amounts of potassium hydroxide solution and the procedure used is otherwise the same, this gives an identical result.

EXAMPLE 3

2,000 parts by volume of a dark brown aqueous solution of a carboxylation melt obtained from reacting potassium 1-naphtholate with carbon dioxide, the solution containing per liter 94 parts of 1-hydroxy-2-naphthoic acid, are brought at 80° C. to pH 6.0 with 30% strength aqueous hydrochloric acid.

3 parts of stearyldimethylbenzylammonium chloride or trioctylmethylphosphonium chloride are added in the form of a 50% strength aqueous solution, the mixture is stirred at 80° C. for 5 minutes, 6 parts of active charcoal are then added, and the resulting suspension is clarified through a heated filter. The clear colorless aqueous filtrate is brought to pH 2 with 78% strength sulfuric acid.

The 1-hydroxy-2-naphthoic acid which precipitates in the course of the pH adjustment is filtered off, washed with water until neutral, and dried. This gives 184 parts of colorless 1-hydroxy-2-naphthoic acid (98% of theory).

94 parts of the 1-hydroxy-2-naphthoic acid thus prepared are dissolved at 35° C. in a mixture of 300 parts of water and 60 parts of 33% strength sodium hydroxide solution. The solution is found to be at pH 6.0–6.5. A 3 hour esterification is carried out at pH 6.5 and an internal temperature of 35° C. by adding 150 parts of diethyl sulfate and, at the same time and dropwise, about 60 parts of 33% strength sodium hydroxide solution.

In the course of the dropwise addition ethyl 1-hydroxide-2-naphthoate precipitates in the form of coarse colorless crystals.

The suspension is stirred at 35° C. for 1 hour, the excess diethyl sulfate is destroyed by adding 3 parts of 33% strength sodium hydroxide solution, the temperature is lowered to 10° C., and the crystals are isolated by filtration.

This gives 210 parts of ethyl 1-hydroxy-2-naphthoate which has a melting point of 48.5°–49° C. and which contains no detectable impurities (purity as determined by potentiometric titration: 99.8°–99.9%; yield: 97.2% of theory, relative to pure 1-hydroxy-2-naphthoic acid started with).

We claim:

1. A process for preparing pure alkyl 1-hydroxy-2-naphthoates of the formula (I)

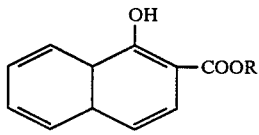

in which R denotes straight-chain or branched alkyl of 1 to 5 carbon atoms, which comprises adjusting, with mineral acid, to pH 5.5–6.5 an aqueous solution of monoalkali and/or dialkali metal salts of 1-hydroxy-2-naphthoic acid obtained by carboxylating an alkali metal 1-naphtholate by the Kolbe-Schmitt method, followed by treatment with water, or by dissolving, in aqueous alkali metal hydroxide solution, 1-hydroxy-2-naphthoic acid prepared in this way but isolated, then adding a surface-active cationic compound (1) of the general formula (II)

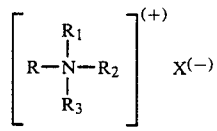

in which R, $R_1$, $R_2$ and $R_3$ each denote identical or different, straight-chain or branched aliphatic radicals of 1 to 30 carbon atoms which are saturated or contain 1, 2 or 3 carbon-carbon double bonds and which can contain 1 to 3 hetero atoms or groupings from the series consisting of —O—,

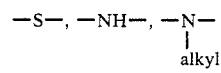

and quaternized nitrogen atoms, and/or carboxamide groups, and which, furthermore, can contain in terminal positions, ionic substituents, or hydroaromatic carbocyclic or cycloaliphatic radicals which each have 4 to 8 ring carbon atoms and can bear aliphatic side chains of 1 to 12 carbon atoms or halogen atoms, or aralkyl radicals where the alkyl radical contains 1 to 30 carbon atoms and the aryl radical is a phenyl or naphthyl radical which can be substituted in the aromatic nucleus by hydroxyl groups, lower alkyl groups, lower alkoxy groups and/or halogen atoms, or aryl radicals which can be substituted on the aromatic nucleus by hydroxyl, lower alkoxy, lower alkyl, carboxamide or sulfonamide groups or halogen atoms, the total number of the carbon atoms of R, $R_1$, $R_2$ and $R_3$ being at least 8 and two or three of the aliphatic radicals R, $R_1$, $R_2$ and $R_3$ on the quaternary nitrogen atom being capable of forming together with the nitrogen atom a heterocyclic ring which may contain double bonds and onto which a benzene nucleus can be fused and in which $X^{(-)}$ represents one equivalent of an inorganic or organic acid, or (2) of the general formula (III)

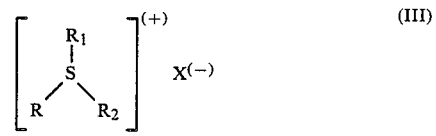

in which R, $R_1$, $R_2$ and $X^{(-)}$ have the meanings mentioned in the definition of formula (II), but where the total number of carbon atoms of R, $R_1$ and $R_2$ is at least 6 and two of the aliphatic radicals R, $R_1$ and $R_2$ together with the sulfur atom can form a heterocyclic ring which may contain double bonds, or (3) of the general formula (IV)

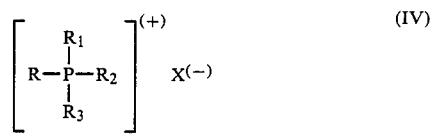

in which R, $R_1$, $R_2$, $R_3$ and $X^{(-)}$ have the meanings given in the definition of formula (II), where the total number of carbon atoms of R, $R_1$, $R_2$ and $R_3$ is at least 8 and two or three of the aliphatic radicals R, $R_1$, $R_2$ and $R_3$ can form together with the phosphorus atom a heterocyclic ring which may contain double bonds, in each case in an amount of 0.5 to 5% by weight relative to the amount of 1-hydroxy-2-naphthoic acid present in the solution, separating or filtering off the solid or liquid precipitates quantitatively formed from the resins present at temperatures of 50° C. to 100° C. if desired after addition of adsorbents and/or filtering aids and esterifying with dialkyl sulfate the pure monoalkali metal salt of 1-hydroxy-2-naphthoic acid present in aqueous solution at pH 5.5–6.5 and temperatures between 30° and 80° C.

* * * * *